(12) United States Patent
Alvarez-Ruiz et al.

(10) Patent No.: US 10,077,458 B2
(45) Date of Patent: Sep. 18, 2018

(54) MICROBIOLOGICAL PROCESS

(71) Applicant: GlaxoSmithKline Intellectual Property Development Limited, Brentford, Middlesex (GB)

(72) Inventors: Emilio Alvarez-Ruiz, Madrid (ES); Andrew John Collis, Ulverston (GB); Alison Sarah Dann, Worthing (GB); Andrew Peter Fosberry, Stevenage (GB); Sarah Jane Ready, Stevenage (GB); Maria Jesus Vazquez Muniz, Madrid (ES)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/118,924

(22) PCT Filed: Feb. 17, 2015

(86) PCT No.: PCT/EP2015/053282
§ 371 (c)(1),
(2) Date: Aug. 15, 2016

(87) PCT Pub. No.: WO2015/121488
PCT Pub. Date: Aug. 20, 2015

(65) Prior Publication Data
US 2016/0355856 A1  Dec. 8, 2016

(30) Foreign Application Priority Data

Feb. 17, 2014 (EP) .................................... 14382054

(51) Int. Cl.
*A61K 31/445* (2006.01)
*C12P 17/12* (2006.01)
*C12R 1/465* (2006.01)
*C12P 19/26* (2006.01)
*C07D 211/46* (2006.01)
*C12N 1/20* (2006.01)

(52) U.S. Cl.
CPC ............ *C12P 17/12* (2013.01); *A61K 31/445* (2013.01); *C07D 211/46* (2013.01); *C12N 1/20* (2013.01); *C12P 19/26* (2013.01); *C12R 1/465* (2013.01); *Y02A 50/481* (2018.01)

(58) Field of Classification Search
CPC .............................. A61K 31/445; C12P 17/12
USPC ......................................................... 514/315
See application file for complete search history.

(56) References Cited

FOREIGN PATENT DOCUMENTS

GB          2086394 A      5/1982
WO    WO 2008/045015 A1   4/2008

OTHER PUBLICATIONS

Lees, et al., *Bioorganic Chemistry*, 20(2):173-179 (1992).
Miyake, et al., *Agricultural and Biological Chemistry*, 52(7):1649-1654 (1988).
Ruiz, et al., *Tetrahedron Letters*, 40(10):2021-2024 (1999).
International Search Report, which issued on International Application No. PCT/EP2015/053282 is submitted herewith.

*Primary Examiner* — Kevin E Weddington
(74) *Attorney, Agent, or Firm* — Elizabeth J. Hecht; Edward R. Gimmi

(57) ABSTRACT

A process for the microbial synthesis of migalastat, specifically a process for the production of migalastat comprising culturing a microorganism under conditions such that at least one imino sugar is produced and detecting and/or isolating an imino sugar produced by said microorganism, and the microorganisms used in this process. The invention also comprises migalastat produced according to the above method and pharmaceutical compositions and uses thereof.

3 Claims, No Drawings

MICROBIOLOGICAL PROCESS

This application is a 371 of International Application No. PCT/EP2015/053282, filed 17 Feb. 2015 which claims the priority of EP 14383054.6 filed 17 Feb. 2014, both of which are incorporated herein by reference in their entireties.

BACKGROUND OF THE INVENTION

This invention relates to a process for making the imino sugar D-1-deoxygalactonojirimycin (DGJ) the generic name of which is migalastat.

Migalastat can be used in the treatment of Fabry disease (Fan et al., *Nat Med* 1999 5:1, 112-5). There are several chemical routes to migalastat disclosed in the literature. Santoyo-Gonzalez et al., *Synlett* 1999 593-595 describes the synthesis of migalastat from D-galactose, by a chemical route comprising eight steps including undesirable azide chemistry. A twelve-step chemical route to migalastat starting from 1,2:5,6-di-O-isopropylidene-α-D-glucofuranose is described by Legler & Pohl, *Carbohydr. Res.*, 155 (1986) 119-129. The final step of this process involves converting galactostatin bisulfite adduct to migalastat. Migalastat has also been synthesised from galactopyranose (Bernotas et al., *Carbohydr. Res.* 167 (1987) 305-11); L-tartaric acid (Aoyagi et al., *J. Org. Chem.* 56 (1991) 815); quebrachoitol (Chida et al., *J. Chem. Soc., Chem Commun.* 1994, 1247); galactofuranose (Paulsen et al., *Chem. Ber.* 1980, 113, 2601); benzene (Johnson et al., *Tetrahedron Lett.* 1995, 36, 653); arabino-hexos-5-ulose (Barili et al., Tetrahedron 1997, 3407); 5-azido-1,4-lactones (Shilvock et al., Synlett, 1998, 554); deoxynojirimycin (Takahashi et al., *J. Carbohydr. Chem.* 17 (1998) 117); acetylglucosamine (Heightman et al., *Helv. Chim. Acta* 1995, 78, 514); myo-inositol (Chida N, et al., *Carbohydr. Res.* 1992 Dec. 31; 237: 185-94); dioxanylpiperidene (Takahata et al., *Org. Lett.* 2003; 5(14); 2527-2529); and (E)-2,4-pentadienol (Martin et al., *Org Lett.* 2000 January; 2(1):93-5, Hughes et al., *Nat Prod Rep.* 1994 April; 11(2):135-62). WO2008/045015 (Amicus Therapeutics, Inc) describes another chemical process for the preparation of migalastat.

Problems with the existing, chemical processes to migalastat are that they are costly, require at least an eight stage process, and include potentially hazardous azidation chemistry. It would be beneficial if migalastat could be produced by a more cost effective and sustainable process. Fermentation processes are well established in industry as a means to produce biological molecules such as antibiotics, amino acids and vitamins at large scale and relatively low cost (Atkinson, & Mavittma, Biochemical Engineering and Biotechnology Handbook, 2nd Edition, New York, Stockton Press, 1991). Although galactostatin has previously been isolated as its bisulfite adduct from the culture broth of *Streptomyces lydicus* PA-5726 (Miyake and Ebata, Agric. Biol. Chem., 52(7), 1649-1654 (1988)), hitherto no known microorganisms have been identified as producing migalastat.

BRIEF SUMMARY OF THE INVENTION

The present invention relates to a process for the microbial synthesis of migalastat. In particular, it has been discovered that certain naturally occurring microorganisms produce migalastat or precursors thereof.

In one aspect the invention provides a process for the production of migalastat comprising culturing a microorganism under conditions such that at least one imino sugar is produced and detecting and/or isolating an imino sugar produced by said microorganism. In another aspect the invention provides a process for the production of migalastat comprising the steps of a. culturing a microorganism under conditions such that at least one imino sugar is produced, b. detecting and/or recovering an imino sugar produced by said microorganism, and c. if said detected and/or recovered imino sugar is not migalastat, converting said detected and/or isolated imino sugar to migalastat.

In another aspect the invention provides microorganisms utilized in the above methods.

In another aspect the invention provides migalastat produced according to the above methods.

In another aspect the invention provides pharmaceutical compositions comprising migalastat produced according to the above methods.

In another aspect the invention provides methods of treatment using migalastat produced according to the above methods.

The invention also provides an assay method for identifying microorganisms producing migalastat and/or precursors thereof.

DETAILED DESCRIPTION

The present invention is based on the discovery of naturally occurring microorganisms which produce migalastat and/or precursors thereof, and the use of an essentially microbial process route to migalastat.

"Migalastat" refers to 1-deoxygalactonojirimycin (DGJ) which is (2R,3S,4R,5S)-2-(hydroxymethyl) piperidine-3,4,5-triol. As used herein, reference to "migalastat", "1-deoxygalactonojirimycin" or "DGJ" throughout includes both the free base and any salt forms of the same including the hydrochloride salt unless the context indicates otherwise. The hydrochloride salt of migalastat is known as migalastat hydrochloride. References to migalastat also include derivatives of migalastat e.g. N-acetyl migalastat.

"Galactostatin" refers to galactonojirimycin which is 6-(hydroxymethyl)-2,3,4,5-piperidinetetrol. As used herein reference to "galactostatin" throughout includes both the free base and any salt forms of the same including the bisulphite adduct unless the context indicates otherwise. References to galactostatin also include derivatives of galactostatin e.g. N-acetyl galactostatin.

"Imino sugar" means any analogue of a sugar having a nitrogen atom at the position of the endocyclic oxygen atom. Imino sugars which may be produced and detected in accordance with the present invention may have the following formula:

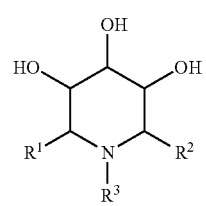

wherein $R^1$ is H or OH; and $R^2$ is H, $CH_3$ or $CH_2OH$; and $R^3$ is independently H or a substituted or unsubstituted $C_1$-$C_{12}$ alkyl, $C_2$-$C_{12}$ alkenyl, $C_2$-$C_{12}$ alkynyl, $C_5$-$C_6$ cycloalkyl, $C_5$-$C_{12}$ cycloalkenyl, $C_5$-$C_{12}$ aryl, $C_4$-$C_{12}$ heteroaryl, $C_6$-$C_{12}$ arylalkyl, $C_4$-$C_{12}$ heterocyclyl, $C_6$-$C_{12}$ hetero-cyclic-alkyl, $C_5$-$C_{12}$ heteroarylalkyl or a $C_2$-$C_{12}$ acyl. Example imino sugars are galactostatin, nojirimycin and mannojirimycin and their deoxy forms migalastat, 1-deoxynojirimycin and 1-deoxymannojirimycin. The term "imino sugar" also includes any biosynthetic precursors of the above named imino sugars, which may be cyclic or linear. The term "imino sugar" also includes open chain forms of the above named imino sugars and both the free base and any salt forms of the above named imino sugars, including adducts (e.g. bisulphite adduct) unless the context indicates otherwise.

Various aspects of the invention are described in further detail in the following subsections.

1. Identification of Suitable Microorganisms

In one aspect the invention provides a process for the production of migalastat comprising culturing a microorganism under conditions such that at least one imino sugar is produced and detecting and/or isolating an imino sugar produced by said microorganism. In one embodiment, an imino sugar is detected. In another embodiment an imino sugar is isolated.

In one embodiment, an imino sugar detected and/or isolated is migalastat or a derivative thereof. In another embodiment an imino sugar detected and/or isolated is galactostatin or a derivative thereof.

In another aspect, the invention provides a process for the production of migalastat comprising culturing a microorganism under conditions such that migalastat is produced.

In another aspect, the invention provides the use of galactostatin produced by a process comprising culturing a microorganism under conditions such that galactostatin is produced, in the manufacture of migalastat.

In another aspect, the invention provides a process for the production of migalastat comprising the steps of a. culturing a microorganism under conditions such that at least one imino sugar is produced, b. detecting and/or recovering an imino sugar produced by said microorganism, and c. if said detected and/or recovered imino sugar is not migalastat, converting said detected and/or isolated imino sugar to migalastat.

The microorganism is suitably a bacterium, for example a Gram positive bacterium. For example, the microorganism is suitably an Actinobacterium. Suitable microorganisms belong to the Streptomycetaceae family, for example microorganisms of *Streptomyces* or *Streptoverticillium* genera. Alternatively, suitable microorganisms belong to a genus selected from the group consisting of *Bacillus, Paenibacillus, Cornyebacterium, Lactobacillus* and Lactococci. The microorganism is suitably a Gram negative bacterium. For example, suitable microorganisms belong to a genus selected from the group consisting of *Salmonella, Escherichia, Klebsiella, Serratia* and *Proteus*. In one embodiment the microorganism is a bacterium selected from the group consisting of: *Streptomyces, Bacillus; Paenibacillus, Cornyebacterium; Lactobacillus*; Lactococci; *Salmonella; Escherichia; Klebsiella; Serratia*; and *Proteus*. In one embodiment the microorganism is of the genus *Escherichia*. In one embodiment the microorganism is *Escherichia coli*.

Examples of suitable bacteria are *Streptomyces lydicus, Streptomyces subrutilus, Streptomyces lavendulae, Streptomyces anulatus* etc. Specific strains of bacteria which may be used in this aspect of the invention include *Streptomyces* sp BTA530 (NCIMB 42142, deposited 18 Apr. 2013) and *Streptomyces lydicus* ATCC319075. In one embodiment the bacterium comprises *Streptomyces* bacteria selected from the group consisting of: *Streptomyces lydicus; Streptomyces subrutilus; Streptomyces lavendulae; Streptomyces anulatus; Streptomyces* sp BTA530 (NCIMB 42142); and *Streptomyces lydicus* ATCC319075.

Suitable microorganisms for use in these aspects of the invention may be identified by screening for the presence of imino sugars in the culture broth of microorganisms. Imino sugars may be detected in the culture broth using glycosidase assays from commercial sources.

For example, migalastat and galactostatin are both reversible competitive inhibitors of α-galactosidase A, and accordingly these imino sugars may be detected in culture broth using any well accepted assay for α-galactosidase A activity. Quantification of migalastat and galactostatin in the culture broth may then be carried out by well accepted analytical chemistry techniques such as LC/MS.

Microorganisms identified as being suitable for use in the processes of the invention may be further improved for enhanced production of imino sugars. For example, a microorganism identified as being suitable for use in the processes of the invention may be subjected to random screening for enhanced production of an imino sugar such as galactostatin or migalastat. Suitable random screening methodology which may be used for industrial strain improvement is known in the art, for example R. T. Rowlands (1984) "Industrial strain improvement: mutagenesis and random screening procedures" Enzyme and Microbial Technology 6(1) 3-10. One such randomly mutated microorganism is *Streptomyces* sp mutant BTM4 (NCIMB 42358). This strain was selected by screening for increased production of migalastat within a population of single colony isolates derived from *Streptomyces* sp BTA530 (NCIMB 42142) as survivors of mutagenic irradiation with ultraviolet light.

Isolated *Streptomyces* sp BTA530 (NCIMB 42142) forms an aspect of the invention. *Streptomyces* sp mutant BTM4 (NCIMB 42358) forms another aspect of the invention. A further aspect of the invention is the use of Isolated *Streptomyces* sp BTA530 (NCIMB 42142) or the use of *Streptomyces* sp mutant BTM4 (NCIMB 42358) in a process for producing migalastat.

2. Culturing and Fermenting Microorganisms

The term "culturing" includes maintaining and/or growing a living microorganism (e.g., maintaining and/or growing a culture or strain). In the performance of the process of the invention, microorganisms may be cultured in liquid media. Alternatively, microorganisms may be cultured in solid media or semi-solid media.

2.1 Culture Media

In one embodiment of the invention, microorganisms are cultured in media (e.g., a sterile, liquid medium) comprising nutrients essential or beneficial to the maintenance and/or growth of the microorganisms. Examples of nutrients include carbon sources or carbon substrate, nitrogen sources, phosphorous sources, trace elements and growth factors.

Suitable carbon sources or carbon substrate include carbohydrate, hydrocarbons, oils, fats, fatty acids, organic acids and alcohols. Examples of suitable carbon sources are glycerol, dextrin, maltodextrin, rape seed oil, lactose, galactose, tagatose, glucose, lactulose and dextrose (such as Meritose i.e. dextrose monohydrate).

In one embodiment, lactose is used as a carbon source. In one embodiment, lactose is used as a carbon source to a final concentration of 0-50% w/v, for example 0-30%, for example 0-10%, for example 1%, 2%, 3%, 4%, 5%, 6%, 7%, 8% or 9%. In one embodiment the culture medium comprises lactose to a final concentration of about 1-3%, for example about 2%. In one embodiment the culture medium comprises lactose to a final concentration of about 1.7% w/v. In another embodiment, lactulose is used as a carbon source. In one embodiment, lactulose is used as a carbon source to a final concentration of 0-50% w/v, for example 0-30%, for example 0-10%, for example 1%, 2%, 3%, 4%, 5%, 6%, 7%, 8% or 9%. In one embodiment the culture medium comprises lactulose to a final concentration of about 1-3%, for example about 2%. In one embodiment the culture medium comprises lactulose to a final concentration of about 1.7% w/v. In another embodiment, the culture medium comprises glycerol. In one embodiment, the culture medium comprises glycerol to a final concentration of 0-50% w/v, for example 0-30%, for example 0-10%, for example 1%, 2%, 3%, 4%, 5%, 6%, 7%, 8% or 9%. In one embodiment the culture medium comprises glycerol to a final concentration of about 3-5%, for example about 4%.

In another embodiment, galactose is used as a carbon source. In one embodiment, the culture medium comprises galactose to a final concentration of 0-50% w/v, for example 0-30%, for example 0-10%, for example 1%, 2%, 3%, 4%, 5%, 6%, 7%, 8% or 9%. In one embodiment the culture medium comprises galactose to a final concentration of about 1-3%, for example about 2%. In one embodiment the culture medium comprises galactose to a final concentration of about 1.7% w/v.

The carbon source(s) may be selected to influence the production of the desired imino sugar in the processes of the present invention. For example, in the processes of the present invention the inventors have discovered that the use of a culture medium comprising lactose enhances the production of migalastat by the imino sugar producing microorganism. The use of a culture medium which does not comprise lactose favours the production by the microorganism of galactostatin. In one embodiment of the invention, the process for the production of migalastat comprises culturing a microorganism in a medium comprising lactose.

Culture media may suitably comprise more than one source of carbon. In one embodiment microorganisms are cultured in the presence of one or more than one carbon source selected from glycerol, dextrin, maltodextrin, rape seed oil, lactose, galactose, tagatose, glucose and lactulose. In one embodiment the culture medium comprises lactose and dextrose. In one embodiment the culture medium comprises lactulose and dextrose. In one embodiment the culture medium comprises lactose and dextrose and glycerol. In one embodiment the culture medium comprises lactulose and dextrose and glycerol. In one embodiment the culture medium comprises dextrose and glycerol.

In one embodiment, the culture medium comprises lactose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%. In one embodiment the culture medium comprises lactose to a final concentration of about 1-3%, for example about 2% and dextrose to a final concentration of about 1-3%, for example about 1.5%. In one embodiment the culture medium comprises lactose to a final concentration of about 1.7% w/v and dextrose to a final concentration of about 1.5% w/v.

In one embodiment, the culture medium comprises lactulose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%. In one embodiment the culture medium comprises lactulose to a final concentration of about 1-3%, for example about 2% and dextrose to a final concentration of about 1-3%, for example about 1.5%. In one embodiment the culture medium comprises lactulose to a final concentration of about 1.7% w/v and dextrose to a final concentration of about 1.5% w/v.

In one embodiment, the culture medium comprises galactose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%. In one embodiment the culture medium comprises galactose to a final concentration of about 1-3%, for example about 2% and dextrose to a final concentration of about 1-3%, for example about 1.5%. In one embodiment the culture medium comprises galactose to a final concentration of about 1.7% w/v and dextrose to a final concentration of about 1.5% w/v.

In one embodiment, the culture medium comprises lactose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%, and glycerol to a final concentration of 0-50% w/v, for example 0-30%, for example 0-10%, for example 1%, 2%, 3%, 4%, 5%, 6%, 7%, 8% or 9%. In one embodiment the culture medium comprises lactose to a final concentration of about 1-3%, for example about 2% and dextrose to a final concentration of about 1-3%, for example about 1.5%, and glycerol to a final concentration of about 3-5%, for example about 4%. In one embodiment the culture medium comprises lactose to a final concentration of about 1.7% w/v and dextrose to a final concentration of about 1.5% w/v and glycerol to a final concentration of about 4%.

In one embodiment, the culture medium comprises lactulose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%, and glycerol to a final concentration of 0-50% w/v, for example 0-30%, for example 0-10%, for example 1%, 2%, 3%, 4%, 5%, 6%, 7%, 8% or 9%. In one embodiment the culture medium comprises lactulose to a final concentration of about 1-3%, for example about 2% and dextrose to a final concentration of about 1-3%, for example about 1.5%, and glycerol to a final concentration of about 3-5%, for example about 4%. In one embodiment the culture medium comprises lactulose to a final concentration of about 1.7% w/v and dextrose to a final concentration of about 1.5% w/v and glycerol to a final concentration of about 4%.

In one embodiment, the culture medium comprises galactose to a final concentration of 0-50% w/v, for example 0-30%, for example 0-10%, for example 1%, 2%, 3%, 4%, 5%, 6%, 7%, 8% or 9%, and dextrose to a final concentration of 0-50% w/v, for example 0-30%, for example 0-10%, for example 1%, 2%, 3%, 4%, 5%, 6%, 7%, 8% or 9%, and glycerol to a final concentration of 0-50% w/v, for example 0-30%, for example 0-10%, for example 1%, 2%, 3%, 4%, 5%, 6%, 7%, 8% or 9%. In one embodiment the culture medium comprises galactose to a final concentration of about 1-3%, for example about 2% and dextrose to a final concentration of about 1-3%, for example about 1.5%, and glycerol to a final concentration of about 3-5%, for example about 4%. In one embodiment the culture medium comprises galactose to a final concentration of about 1.7% w/v and dextrose to a final concentration of about 1.5% w/v and glycerol to a final concentration of about 4%.

In one embodiment, the culture medium comprises dextrose to a final concentration of 0-50% w/v, for example 0-30%, for example 0-10%, for example 1%, 2%, 3%, 4%, 5%, 6%, 7%, 8% or 9%, and glycerol to a final concentration of 0-50% w/v, for example 0-30%, for example 0-10%, for example 1%, 2%, 3%, 4%, 5%, 6%, 7%, 8% or 9%. In one embodiment the culture medium comprises dextrose to a final concentration of about 1-3%, for example about 1.5%, and glycerol to a final concentration of about 3-5%, for example about 4%. In one embodiment the culture medium comprises dextrose to a final concentration of about 1.5% w/v and glycerol to a final concentration of about 4%.

Suitable nitrogen sources include soy protein (such as Arcon F), cotton seed flour, CSL (corn steep liquor), peptone, yeast extracts, meat extracts, malt extracts, ammonium sulfate, ammonium chloride, casamino acids and ammonium phosphate. Cotton seed flour is available from a variety of commercial sources including ProFlo, Pharmamedia, Sigma. In one embodiment the nitrogen source is soy protein. In one embodiment, the culture medium comprises soy protein to a final concentration of 0-50% w/v, for example 0-30%, for example 0-10%, for example 1%, 2%, 3%, 4%, 5%, 6%, 7%, 8% or 9%. In one embodiment the culture medium comprises soy protein to a final concentration of about 1-5%, for example about 2.5%. In one embodiment the nitrogen source is cotton seed flour. In one embodiment, the culture medium comprises cotton seed flour to a final concentration of 0-50% w/v, for example 0-30%, for example 0-10%, for example 1%, 2%, 3%, 4%, 5%, 6%, 7%, 8% or 9%. In one embodiment the culture medium comprises cotton seed flour to a final concentration of about 1-5%, for example about 2.5%. In one embodiment the nitrogen source is CSL. In one embodiment, the culture medium comprises CSL to a final concentration of 0-50% w/v, for example 0-30%, for example 0-10%, for example 0.5%, 1%, 2%, 3%, 4%, 5%, 6%, 7%, 8% or 9%. In one embodiment the culture medium comprises CSL to a final concentration of about 0.5%.

Culture media may suitably comprise more than one source of nitrogen. In one embodiment microorganisms are cultured in media comprising one or more than one nitrogen source selected from soy protein (such as Arcon F), cotton seed flour, CSL (corn steep liquor), peptone, yeast extracts, meat extracts, malt extracts, ammonium sulfate, ammonium chloride, casamino acids and ammonium phosphate. In one embodiment the culture medium comprises cotton seed flour and CSL. In one embodiment, the culture medium comprises cotton seed flour to a final concentration of 0-50% w/v, for example 0-30%, for example 0-10%, for example 1%, 2%, 3%, 4%, 5%, 6%, 7%, 8% or 9% and CSL to a final concentration of 0-50% w/v, for example 0-30%, for example 0-10%, for example 0.5%, 1%, 2%, 3%, 4%, 5%, 6%, 7%, 8% or 9%. In one embodiment the culture medium comprises cotton seed flour to a final concentration of about 1-5%, for example about 2.5% and CSL to a final concentration of about 0.5%.

Suitable phosphorus sources include phosphoric acid, sodium and potassium salts thereof. Suitable trace elements include magnesium, iron, manganese, calcium, copper, zinc, boron, molybdenum, potassium chloride and/or cobalt salts.

Examples of suitable trace elements are magnesium sulphate, ferrous sulphate, zinc chloride, cupric chloride, calcium chloride, calcium carbonate, magnesium chloride, iron chloride, sodium chloride, and manganese sulphate. In one embodiment microorganisms are cultured in media comprising calcium carbonate.

Suitable growth factors include amino acids (including salts thereof) such as glutamic acid, monosodium glutamate and leucine; vitamin B6 and citric acid.

In one embodiment of the process aspects of the invention, the medium comprises soy protein concentrate (such as soy protein concentrate Arcon F), for example 0-5%. In one embodiment the medium comprises dextrin (Soluble starch), for example 0-4%. In one embodiment the medium comprises magnesium sulphate ($MgSO_4.7H2O$), for example 0-0.7%. In one embodiment the medium comprises $KH_2PO_4$, for example 0-0.8%. In one embodiment the medium comprises rape seed oil, for example 0-0.2%. In one embodiment the medium comprises calcium carbonate, for example 0-0.12%. In one embodiment the medium comprises an antifoam agent such as Foam Doctor, for example 0-0.4%. In one embodiment the medium comprises cottonseed flour, for example 0-5%. In one embodiment the medium comprises glucose, for example 0-3%. In one embodiment the medium comprises lactose, for example 0-7%. In one embodiment the medium comprises lactulose, for example 0-7%. In one embodiment the medium comprises glycerol, for example 0-8%. In one embodiment the medium comprises CSL, for example 0-1%. In one embodiment the medium comprises any one or more of soy protein concentrate (such as soy protein concentrate Arcon F), dextrin (Soluble starch), Magnesium sulphate ($MgSO_4.7H2O$), $KH_2PO_4$, rape seed oil, calcium carbonate, an antifoam agent, cottonseed flour, glucose, lactose, lactulose, glycerol, and CSL.

In one embodiment the medium comprises soy protein concentrate (such as soy protein concentrate Arcon F), dextrin (Soluble starch), Magnesium sulphate ($MgSO_4.7H2O$), $KH_2PO_4$, rape seed oil, calcium carbonate and an antifoam agent. In another embodiment the medium comprises cottonseed flour, glucose, lactose, glycerol, CSL, calcium carbonate and an antifoam agent. In another embodiment the medium comprises cottonseed flour, lactulose, Meritose (i.e.dextrose), glycerol, CSL, calcium carbonate and an antifoam agent.

2.2 Culture Conditions

In the processes of the invention, microorganisms may be cultured under controlled pH. The term "controlled pH" includes any pH which results in production of the desired product (e.g. migalastat or galactostatin). In one embodiment microorganisms are cultured at a pH of between 6.0 and 9.0. In another embodiment, microorganisms are cultured at a pH of between 7.0 and 8.0. In another embodiment, microorganisms are cultured at a pH of about 7. In another embodiment, microorganisms are cultured at a pH of about 7.2 or about 7.7 or about 7.8.

In one embodiment pH is regulated e.g. maintained during the culture of the microorganisms. In one embodiment the pH was maintained between 0 and 50 hours, in another embodiment the pH was maintained between 50 and 220 hours. In another embodiment the pH was maintained between 0-220 hours.

Suitably, the initial pH of the culture may be adjusted to a suitable level, but is not regulated or maintained thereafter during the process of the invention. In a related embodiment the initial pH was adjusted to between 6.5 and 7.60 but not regulated thereafter. The desired pH may be initially adjusted and optionally thereafter regulated or maintained by any number of methods known to those skilled in the art. Examples of suitable pH regulants are $H_2SO_4$, Ammonium hydroxide, Ammonia gas, NaOH, and acetic acid pH regulants. In one embodiment, pH is maintained between pH 7-8. In one embodiment pH is maintained between pH 7-8 using NaOH. In one embodiment, pH is adjusted to pH 7.8. In one embodiment pH is adjusted using NaOH. In one embodiment pH is adjusted to pH 7.8 using NaOH. In another embodiment, pH is adjusted to pH 7.7. In one embodiment pH is adjusted using NaOH. In one embodiment pH is adjusted to pH 7.7 using NaOH. In one embodiment pH is adjusted to pH 7.2. In one embodiment pH is adjusted to pH 7.2 using NaOH.

In the processes of the invention the microorganism may be cultured under controlled aeration. The term 'controlled' includes any aeration which results in production of the desired imino sugar product (e.g. migalastat or galactostatin). Aeration can be suitably controlled by the introduction of sparged sterile air through the culture media and/or by agitation, provided either by mechanical input from a propeller or impeller or similar agitation equipment or by shaking the culture vessel and/or by pressure achieved by regulation of the culture vessel vent. For example, an airlift fermenter may be used.

In one embodiment the microorganism is cultured at an airflow between 0.5 vvm (vessel volume per minute)-1.5 vvm. For example the microorganism of the invention may be suitably cultured at 0.5 vvm, 0.6 vvm, 0.7 vvm, 0.8 vvm, 0.9 vvm, 1.0 vvm, 1.1 vvm, 1.2 vvm, 1.3 vvm, 1.4 vvm, 1.5 vvm. In a related embodiment the aeration is controlled by agitation. In one embodiment agitation tip speed is between 1.0 m/s-6.0 m/s.

In the processes of the present invention microorganisms can be cultured under controlled pressure. The term "controlled pressure" includes any pressure which results in production of the desired imino sugar product (e.g. migalastat or galactostatin). In one embodiment, controlled pressures include pressures between 0.3 Bar and 1.5 Bar. In one embodiment the microorganism is cultured at pressure between 0.3-1.1 Bar. For example the microorganism of the invention may be suitably cultured at a pressure of 0.5 Bar, 0.6 Bar, 0.7 Bar, 0.8 Bar, 0.9 Bar. In a related embodiment the aeration is controlled by shaking the culture vessel. For example the microorganism may suitably be cultured at 180 rpm-280 rpm. For example, the microorganism may suitably be cultured at 200 rpm-240 rpm. For example, the microorganism may suitably be cultured at about 220 rpm. In a related embodiment aeration is controlled by regulating dissolved oxygen levels in the culture media through regulation of agitation and or regulation of airflow. In one embodiment dissolved oxygen is regulated above 10-50%. For example the microorganism of this invention may be suitably cultured at above 10%, 15%, 20% 25%, 30%, 35%, or 40%. For example the microorganism of this invention may be suitably cultured at 10%, 15%, 20% 25%, 30%, 35%, or 40%. For example in the processes of the invention the oxygen level in the culture may be regulated to above 20%.

In the processes of the present invention microorganisms may also suitably be cultured without excess foaming (e.g., via addition of antifoaming agents, such as Foam Doctor).

Moreover, in the processes of the present invention microorganisms can be cultured under controlled temperatures. The term "controlled temperature" includes any temperature which results in production of the desired imino sugar product (e.g. migalastat or galactostatin). In one embodiment, controlled temperatures include temperatures between 15° C. and 35° C. In another embodiment temperatures are between 20° C. and 53° C., for example between 25° C. and 40° C. For example, the microorganisms of the invention may suitably be cultured at 25° C., 26° C., 27° C., 28° C., 29° C., 30° C., 31° C., 32° C., 33° C., 34° C., 35° C. For example, in the processes of the invention the microorganisms may be cultured at about 28° C.

2.3 Culturing Methods

Microorganisms can be cultured (e.g., maintained and/or grown) in liquid media and suitably are cultured, either continuously or intermittently, by conventional culturing methods such as standing culture, test tube culture, shaking culture (e.g., rotary shaking culture, shake flask culture, etc.), aeration spinner culture, or fermentation in a stirred tank or airlift fermenter. In one embodiment, the microorganisms are cultured in shake flasks. In another embodiment, the microorganisms are cultured in a fermenter (e.g. a fermentation process). Fermentation processes of the present invention include, but are not limited to, batch, fed-batch and continuous processes or methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermenter and an equal amount of used or "conditioned" media is simultaneously removed, suitably for recovery of the desired imino sugar product (e.g. migalastat or galactostatin). A variety of such processes have been developed and are well-known in the art.

In one embodiment of the invention, a batch fermentation process is used. In another embodiment, a batch-fed fermentation process is used.

The phrase "culturing under conditions such that at least one imino sugar is produced" includes maintaining and/or growing microorganisms under conditions (e.g., temperature, pressure, pH, viscosity, duration, etc.) appropriate or sufficient to obtain production of at least one imino sugar or to obtain desired yields of at least one imino sugar. For example, culturing is continued for a time sufficient to produce the desired amount of an imino sugar compound (e.g. migalastat or galactostatin or a precursor thereof). Preferably, culturing is continued for a time sufficient to substantially reach suitable production of the compound (e.g., a time sufficient to reach a suitable concentration of migalastat or galactostatin or suitable ratio of migalastat: galactostatin). In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, 144 to 168 hours, 168 to 192 hours, 192 to 216 hours, 216 to 240 hours, 240 to 264 hours, 264 to 288 hours, 288 to 312 hours, 312 to 336 hours, or greater than 336 hours. In yet another embodiment, microorganisms are cultured under conditions such that at least about 0.5 to 10 g/L of compound are produced throughout the fermentation.

Processes of the present invention may include separate seed and final fermentation stages. Alternatively, inoculum spores may be directly inoculated into final stage media. In one embodiment, the process comprises a seed fermentation and a final fermentation. In one embodiment the process does not include a seed fermentation stage. In one embodiment, the process comprises a final fermentation stage without a seed fermentation stage. When separate seed and final fermentation stages are used, in a seed fermentation stage an inoculum is used to seed a seed fermentation medium. This may be achieved by using a spore inoculum or a vegetative inoculum. The seeded fermentation medium may then be incubated under suitable conditions as set out hereinabove. In a final fermentation stage, the seed fermentation is used to inoculate a final stage medium.

In one embodiment of the invention, the process includes an initial seed fermentation stage. In one embodiment of the invention, the process involves a seed fermentation stage and a final fermentation stage. Final stage fermentations typically run for up to 280 hours where as seed stage fermentation stages typically run for up to 72 hours.

2.3.1 Seed Fermentation

Typically, an inoculum will contain spores to give a concentration of $1.5 \times 10^4$ to $2.5 \times 10^5$ spores per ml of culture media. One suitable spore concentration is $6 \times 10^4$ spores per ml of culture media. Suitable media for the seed fermentation stage are as defined hereinabove in section 2.1. In one embodiment, the seed medium comprises soy protein concentrate (such as soy protein concentrate, Arcon F). In one embodiment the seed medium comprises dextrin (soluble starch). In one embodiment the seed medium comprises magnesium sulphate ($MgSO_4.7H_2O$). In one embodiment the seed medium comprises $KH_2PO_4$. In one embodiment the seed medium comprises rape seed oil. In one embodiment the seed medium comprises calcium carbonate. In one embodiment the seed medium comprises an antifoam agent. In one embodiment the seed medium comprises cotton seed flour (a protein source). In one embodiment the seed medium comprises Meritose (dextrose). In one embodiment the seed medium comprises CSL (a protein source).

In one embodiment the seed medium comprises any one or more of soy protein concentrate (such as soy protein concentrate, Arcon F), dextrin (Soluble starch), Magnesium sulphate ($MgSO_4.7H_2O$), $KH_2PO_4$, rape seed oil, calcium carbonate, an antifoam agent, cotton seed flour, Meritose (dextrose) and CSL.

In one embodiment the seed medium comprises soy protein concentrate (such as soy protein concentrate, Arcon F), dextrin (soluble starch), magnesium sulphate ($MgSO_4.7H_2O$), $KH_2PO_4$, rape seed oil, calcium carbonate and an antifoam agent.

In one embodiment the seed medium comprises any one or more or all of soya protein, for example Arcon F, for example 0 to 5%, soluble starch, for example 0 to 4%, Magnesium sulphate, for example 0 to 0.7%, Potassium phosphate, for example 0 to 0.8%, Rape seed oil, for example 0 to 0.2%, Calcium chloride, for example 0 to 0.12%, Magnesium chloride, for example 0 to 0.04%, Sodium chloride, for example 0 to 0.04%, Iron chloride, for example 0 to 0.02%, Zinc chloride, for example 0 to 0.002%, Copper chloride, for example 0 to 0.002%, Manganese sulphate, for example 0 to 0.002%, and an antifoam agent, for example 0 to 0.4%.

In one embodiment the medium used in the seed growth phase comprises any one or more or all of cotton seed flour, for example 0 to 5%, CSL, for example 0 to 1.0%, Lactose, for example 0 to 4%, Glucose, for example 0 to 2.5%, Glycerol, for example 0 to 8%, Calcium carbonate, for example 0 to 1.6%, Magnesium sulphate, for example 0 to 0.2%, and an antifoam agent, for example 0 to 0.2%.

In one embodiment the seed medium comprises cotton seed flour, Meritose (dextrose), dextrin, CSL and calcium carbonate.

In one embodiment the medium used in the seed growth phase comprises any one or more or all of cotton seed flour, for example 0 to 5%, Meritose (dextrose), for example 0 to 3%, dextrin, for example 0 to 8%, CSL, for example 0 to 1.0%, and calcium carbonate, for example 0 to 1.6%.

In another embodiment the seed medium is substantially as set forth in any of the examples herein.

The pH of the seed medium may suitably be adjusted before and/or during the seed fermentation stage. The pH of the seed medium is suitably adjusted as set out in section 2.2 hereinabove. In one embodiment the seed medium is adjusted to a pH of between 7.0 and 8.0, e.g. to a pH of about 7.8. In one embodiment the pH is adjusted using NaOH.

The seed fermentation stage may suitably be carried out under conditions of controlled aeration, as set out in section 2.2 hereinabove. In one embodiment the aeration is controlled by agitation and by the passage of sterile air through the medium.

The seed fermentation stage may suitably be carried out under conditions of controlled temperature as set out in section 2.2 hereinabove. In one embodiment the seed fermentation is carried out at between 15° C. and 35° C. For example, the seed fermentation is carried out at 25° C., 26° C., 27° C., 28° C., 29° C., 30° C., 31° C., 32° C., 33° C., 34° C., or 35° C.

The inoculated seed medium is cultured for a time sufficient to produce the desired biomass for a final fermentation stage. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours.

2.3.2 Final Fermentation

Typically, the final stage medium is inoculated with seed culture at a level between 0.1% and 8% v/v final stage medium start volume.

Suitable media for the final fermentation stage are as defined hereinabove in section 2.1. In one embodiment, the final stage medium comprises cottonseed flour. In another embodiment the final stage medium comprises glucose. In another embodiment the final stage medium comprises lactose. In another embodiment the final stage medium comprises glycerol. In another embodiment the final stage medium comprises CSL. In another embodiment the final stage medium comprises calcium carbonate. In another embodiment the final stage medium comprises an anti foam agent such as Foam Doctor. In another embodiment the final stage medium comprises lactulose. In another embodiment the final stage medium comprises Meritose (dextrose). In another embodiment the final stage medium comprises galactose.

In another embodiment the final stage medium comprises any one or more of cottonseed flour, glucose, lactose, glycerol, CSL, calcium carbonate, an antifoam agent, lactulose and Meritose (dextrose).

In another embodiment the final stage medium comprises cottonseed flour, glucose, lactose, glycerol, CSL, calcium carbonate and an antifoam agent.

In another embodiment the final stage medium comprises cottonseed flour, glucose, lactulose, glycerol, CSL, calcium carbonate and an antifoam agent.

In another embodiment the final stage medium comprises cottonseed flour, glucose, glycerol, CSL, calcium carbonate and an antifoam agent.

In one embodiment the final stage medium comprises any one or more or all of cotton seed flour, for example 0 to 5%, CSL, for example 0 to 1.0%, Lactose, for example 0 to 4%, Glucose, for example 0 to 2.5%, Glycerol, for example 0 to 8%, Calcium carbonate, for example 0 to 1.6%, and an antifoam agent, for example 0 to 0.2%.

In another embodiment the final stage medium comprises cottonseed flour, lactose, Meritose (dextrose), glycerol, CSL, calcium carbonate and an antifoam agent.

In another embodiment the final stage medium comprises any one or more or all of cotton seed flour, for example 0 to 5%, CSL, for example 0 to 1.0%, Lactose, for example 0 to 4%, Meritose (dextrose), for example 0 to 3.0%, Glycerol, for example 0 to 8%, Calcium carbonate, for example 0 to 1.6%, and an antifoam agent, for example 0 to 0.2%.

In another embodiment the final stage medium comprises cotton seed flour, lactulose, Meritose (dextrose), glycerol, CSL, calcium carbonate and Foam Doctor.

In one embodiment the final stage medium comprises any one or more or all of cotton seed flour, for example 0 to 5%, CSL, for example 0 to 1.0%, Lactulose, for example 0 to 4%, Meritose (dextrose), for example 0 to 3.0%, Glycerol, for example 0 to 8%, Calcium carbonate, for example 0 to 1.6%, and an antifoam agent, for example 0 to 0.2%.

In one embodiment the final stage medium comprises any one or more or all of cotton seed flour, for example 0 to 5%, CSL, for example 0 to 1.0%, galactose, for example 0 to 4%, dextrose, for example 0 to 3.0%, Glycerol, for example 0 to 8%, Calcium carbonate, for example 0 to 1.6%, and an antifoam agent, for example 0 to 0.2%.

In another embodiment the final stage medium is substantially as set forth in any of the examples herein.

In another embodiment the production phase (final stage) comprises cultivating the organism in liquid media comprising cotton seed flour, for example 0 to 5%, CSL, for example 0 to 1.0%, Lactose, for example 0 to 4%, Glucose, for example 0 to 3%, Glycerol, for example 0 to 8%, Calcium carbonate, for example 0 to 1.6%, an antifoam agent, for example 0 to 0.2%.

The pH of the final stage medium may suitably be adjusted before and/or during the final fermentation stage. The pH of the final stage medium is suitably adjusted as set out in section 2.2 hereinabove. In one embodiment the final stage medium is adjusted to a pH of between 7.0 and 8.0, e.g. to a pH of about 7.2. In one embodiment the pH is adjusted using NaOH.

The final fermentation stage may suitably be carried out under conditions of controlled aeration, as set out in section 2.2 hereinabove. In one embodiment the aeration is controlled by agitation and by the passage of sterile air through the medium.

The final fermentation stage may suitably be carried out under conditions of controlled temperature as set out in section 2.2 hereinabove. In one embodiment the seed fermentation is carried out at between 15° C. and 35° C. For example, the final stage fermentation is carried out at 25° C., 26° C., 27° C., 28° C., 29° C., 30° C., 31° C., 32° C., 33° C., 34° C., or 35° C. For example, the final stage fermentation is carried out at about 28° C.

The final fermentation stage is cultured for such time sufficient to produce at least one imino sugar. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, 144 to 168 hours, 168 to 192 hours, 192 to 216 hours, 216 to 240 hours, 240 to 264 hours, 264 to 288 hours or greater than 288 hours, for example 280 hours or longer.

3. Detection, Recovery and Isolation of Desired Compounds

In one embodiment of the process aspects of the invention, the microorganism produces migalastat. In another embodiment the microorganism produces galactostatin. In another embodiment the microorganism produces migalastat and galactostatin.

The methodology of the present invention can further include a step of recovering a desired compound (e.g. migalastat or galactostatin). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media are then passed through or over a cation exchange resin to remove cations and then through or over an anion exchange resin to remove inorganic anions and organic acids having stronger acidities than the compound of interest. The isolated imino sugar of interest can subsequently be converted to a salt (e.g., a hydrochloride salt) as described herein.

In one embodiment, the recovery comprises one or more of the following steps:

(a) desludging—using suitable process centrifuge equipment, for example a disc stack centrifuge, broth solids are advantageously removed to facilitate the subsequent filtration stages. This stage may be eliminated depending on the scale and configuration of subsequent filtration equipment, for example broth at harvest may be clarified directly by use of membranes in a flat sheet configuration or, less effectively, spiral wound configuration (b) filtration—suitably a 10-50 kDa molecular weight cut off membrane is used for initial clarification, for example a 10 kDa membrane, ideally in a flat sheet configuration. Any hydrophilic membrane may be used, typically PES, (polyethersulphone) or CA (cellulose acetate). Recovery of the desired imino sugar can be improved by the use of diafiltration to reduce the concentration of the imino sugar in the membrane retentate; waste, stream. Typically, three diafiltration steps are performed, removing a volume of permeate equivalent to the volume of added diafiltrate at each step. Further purification prior to fractionation can be achieved by ultrafiltration of the initial 10 to 50 kDa permeate and any added diafiltrate with 1 kDa molecular weight cut off membrane. Again, recovery of the desired imino sugar can be improved by diafiltration in the 1 kDa system, typically using three diafiltrations in the method already described.

(c) Fractionation for example using a cation exchange resin—In one embodiment the desired amino sugar (e.g. migalastat) is captured on a cation exchange column and eluted from the resin using a step gradient of hydrochloric acid. Between 5 and 25 bed volumes of ultrafiltrate, either from 10 to 50 kDa or 1 kDa processing can be loaded onto the cation exchange resin. Typically, the resin will be packed into a suitable column but the desired product can also be captured by addition of the resin to the ultrafiltrate with agitation and subsequently recovered by filtration on any suitable media and equipment. Suitable resins would typically but not exclusively be of a styrene divinylbenzene copolymer with suitable functional group, for example sulphonic. A suitable particle size for the resin would be one compatible with good flow characteristics when packed in a column, for example 200 to 250 micron. Higher separation efficiencies may be achieved with smaller particle sizes. Conversely for larger resin particles where higher column flow rates may be achieved. Following displacement of the void volume of residual ultrafiltrate the desired imino sugar can be recovered by elution of the resin with dilute solutions of acid, typically hydrochloric acid. Suitable concentrations of acid would be between 0.1 and 0.5 molar. Advantageously, the elution can be performed as a gradient elution facilitating purification of the desired imino sugar. Elution of the cation exchange step can also be performed using other cations; notably $NH_4^+$.

(d) pH adjustment: In one embodiment, pH of pooled fractions from (c) are adjusted to pH 6-7 by addition of a suitable titrant with agitation, for example sodium hydroxide. In a further embodiment pH of pooled fractions from (c) are adjusted using a suitable anion exchange resin. Suitable anion exchange resins include Dow IRA 67 or Dowex marathon WBA. Use of anion exchange resin to adjust the pH advantageously avoids the additional of titrant which leads to an undesirable level of additional inorganics in the liquor.

(e) concentration: this may suitably be carried out by nanofiltration (reverse osmosis) using a membrane sufficiently retentive to concentrate the imino sugar in the retentate. Alternatively, evaporation may be used to concentrate or further concentrate the selected fractions from cation exchange step (c)

(f) conversion to a salt: this may suitably be carried out by the addition of an acid such as concentrated hydrochloric acid. The salt is isolated as a solid after precipitation caused by the addition of an antisolvent such as ethanol. In one embodiment of the process aspects of the invention, migalastat free base is converted to a migalastat salt, for example migalastat HCl.

(g) recrystallisation: in one embodiment this may be carried out by dissolving the migalastat hydrochloride in water and isolating the solid after precipitation caused by the addition of an antisolvent such as ethanol.

In one embodiment, the recovery of migalastat comprises all of the above steps. In another embodiment, the recovery of galactostatin comprises all of the above steps. In one embodiment the recovering step comprises at least one process selected from the group consisting of: desludging; filtration; fractionation; pH adjustment; concentration; conversion to a salt; and recrystallization.

In another embodiment, the imino sugar is "extracted", "isolated" or "purified" such that the resulting preparation is substantially free of other media components (e.g., free of media components and/or fermentation by-products). The language "substantially free of other media components" includes preparations of the desired compound in which the compound is separated from media components or fermentation by-products of the culture from which it is produced. In one embodiment, the preparation has greater than about 80% (by dry weight) of the desired compound (e.g., less than about 20% of other media components or fermentation by-products). In another embodiment the preparation has greater than about 90% of the desired compound (e.g., less than about 10% of other media components or fermentation by-products), In another embodiment the preparation has greater than about 95% of the desired compound (e.g., less than about 5% of other media components or fermentation by-products). In yet another embodiment, the preparation has greater than about 98-99% desired compound (e.g., less than about 1-2% other media components or fermentation by-products). When the desired compound has been derivatized to a salt, the compound may be further free of chemical contaminants associated with the formation of the salt. When the desired compound has been derivatized to an alcohol, the compound may be further free of chemical contaminants associated with the formation of the alcohol.

In an alternative embodiment, the imino sugar is not purified from the microorganism, for example, when the microorganism is biologically non-hazardous (i.e., safe). For example, the entire culture (or culture supernatant) can be used as a source of product (i.e., crude product). In one embodiment, the culture (or culture supernatant) is used without modification. In another embodiment, the culture (or culture supernatant) is concentrated. In yet another embodiment, the culture (or culture supernatant) is dried or lyophilized.

Suitably, a production method of the present invention results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a production method that includes culturing a recombinant microorganism under conditions such that the desired product (e.g., migalastat) is produced at a level greater than 0.5 g/L. In one embodiment of any aspect of the invention, culturing is continued until at least 0.5 g/L imino sugar has been produced. In one embodiment, culturing is continued until at least 1.0 g/L of imino sugar has been produced. In one embodiment, culturing is continued until at least 1.3 g/L of imino sugar has been produced. In one embodiment, culturing is continued until at least 1.5 g/L of imino sugar has been produced. In one embodiment, culturing is continued until at least 2.0 g/L of imino sugar has been produced. In one embodiment, culturing is continued until at least 2.4 g/L of imino sugar has been produced. In one embodiment, culturing is continued until at least 1.0 g/L of migalastat has been produced. In one embodiment, culturing is continued until at least 1.3 g/L of migalastat has been produced. In one embodiment, culturing is continued until at least 1.5 g/L of migalastat has been produced. In one embodiment, culturing is continued until at least 2.0 g/L of migalastat has been produced. In one embodiment, culturing is continued until at least 2.4 g/L of migalastat has been produced. In one embodiment, culturing is continued until at least 1.0 g/L of galactostatin has been produced. In one embodiment, culturing is continued until at least 1.3 g/L of galactostatin has been produced. In one embodiment, culturing is continued until at least 1.5 g/L of galactostatin has been produced. In one embodiment, culturing is continued until at least 2.0 g/L of galactostatin has been produced. In one embodiment, culturing is continued until at least 2.4 g/L of galactostatin has been produced.

Suitably the microorganisms of the present invention are provided with (i.e. fed) at least one biosynthetic enhancer such that migalastat is produced. The term "biosynthetic enhancer" or "enhancer" includes an agent or compound which, when provided to, brought into contact with, or included in the culture medium of a microorganism, serves to enhance or increase biosynthesis of e.g. migalastat. The term "biosynthetic enhancer" or "enhancer" includes within its scope "biosynthetic precursors" or "precursors". In one aspect the present invention provides a process for the production of migalastat, comprising culturing an iminosugar producing bacterium in the presence of a biosynthetic enhancer.

Suitable imino sugar producing bacteria may be identified by culturing bacteria and screening for the presence of imino sugars in the culture broth. Imino sugars may be detected in the culture broth using glycosidase assays from commercial sources, as set out above in section 1. Suitable bacteria for use in this aspect of the invention are as set out in section 1 above and include *Streptomyces* bacteria selected from the group consisting of: *Streptomyces lydicus*; *Streptomyces subrutilus*; *Streptomyces lavendulae*; *Streptomyces anulatus*; *Streptomyces* sp BTA530 (NCIMB 42142); and *Streptomyces lydicus* ATCC319075. The culture media, conditions and methods described in section 2 are suitable for use in this aspect of the invention.

Suitable bioenhancers include any added substance that specifically drives the production of the desired imino sugars in the processes of the present invention, rather than just the survival and replication of the microorganism being cultured. For example, in one embodiment, the biosynthetic enhancer or enhancer is lactose. In another embodiment, the biosynthetic enhancer or enhancer is lactulose The amount of biosynthetic enhancer (e.g. lactose, lactulose) added is preferably an amount that results in a concentration in the culture medium sufficient to enhance productivity of the microorganism (e.g., a concentration sufficient to enhance production of migalastat). The terms "excess lactose" and "excess lactulose" include lactose or lactulose levels increased or higher that those routinely utilized for culturing the microorganism in question. Accordingly, excess lactose levels can include levels of up to 50%, for example 1-10%, for example 4%. Biosynthetic enhancers of the present invention can be added in the form of a concentrated solution or suspension (e.g., in a suitable solvent such as water or buffer) or in the form of a solid (e.g., in the form of a powder). Moreover, biosynthetic enhancers of the present invention can be added as a single aliquot, continuously or intermittently over a given period of time.

In the embodiments of the invention in which a microorganism produces galactostatin, galactostatin may be converted to migalastat. In one embodiment, in the processes of the invention wherein said conditions are suitable for said bacteria to produce galactostatin, the process comprises detecting galactostatin in the culture and converting said galactostatin to migalastat. In one embodiment, galactostatin may be converted to migalastat in culture. In antoher embodiment, galactostatin is isolated before being converted to migalastat. In one embodiment, conversion of galactostatin may be carried out via chemical conversion. For example, galactostatin can be converted to DGJ by catalytic hydrogenation with platinum catalyst or chemical reduction with $NaBH_4$. A suitable method is described in Legler & Pohl, *Carbohydr. Res.*, 155 (1986) 119-129. In this embodiment galactostatin may be isolated before chemical conversion to migalastat. In another embodiment galactostatin is not isolated before chemical conversion to migalastat.

In another embodiment, conversion of galactostatin to migalastat may be carried out via biotransformation. This may suitably be carried out using a biotransformation microorganism. A "biotransformation microorganism" is any microorganism which contains the enzymes to convert galactostatin to migalastat. Suitable biotransformation microorganisms may be identified by screening for the presence of migalastat in the culture broth of microorganisms cultured in a medium containing galactostatin. The biotransformation microorganism may be a microorganism which is already known to produce imino sugars. Alternatively, the microorganism may not already be known to produce imino sugars. The biotransformation microorganism is suitably a Gram positive bacterium. For example, the microorganism is suitably an Actinobacterium. Suitable microorganisms belong to the Streptomycetacaeae family, for example microorganisms of *Streptomyces* or *Streptoverticillium* genera. Alternatively, suitable microorganisms belong to a genus selected from the group consisting of *Bacillus*, *Paenibacillus*, *Cornyebacterium*, *Lactobacillus* and Lactococci.

The biotransformation microorganism is suitably a Gram negative bacterium. For example, suitable microorganisms belong to a genus selected from the group consisting of *Salmonella*, *Escherichia*, *Klebsiella*, *Serrtia* and *Proteus*. In one embodiment the microorganism is of the genus *Escherichia*. In one embodiment the microorganism is *Escherichia coli*. In another embodiment the microorganism is a microbial eukaryote. In one embodiment the microorganism is a fungus. In one embodiment, the microorganism is of the genus *Saccharomyces*. For example *Saccharomyces cerevisiae*.

In one embodiment of this aspect of the invention, the biotransformation microorganism is *Streptomyces* sp. In another embodiment, the biotransformation microorganism is *Bacillus* sp. In another embodiment, the biotransformation microorganism is *Streptomyces subrutilus*, *Bacillus atrophaeus* or *Streptomyces clavuligerus*. Specific strains of bacteria which may be used in this aspect of the invention include *Streptomyces clavuligerus* ATCC 27064, which has been discovered by the inventors to be capable of the biotransformation of one imino sugar to another.

Biotransformation may also suitably be carried out by other means e.g. plant cells in culture. Suitable plant cells in culture may include plant cells from *Morus alba* (mulberry) or *Commelina communis* (dayflower).

In one embodiment galactostatin is isolated before biotransformation to migalastat. In another embodiment galactostatin is not isolated before biotransformation to migalastat.

If migalastat is to be isolated and used in the salt form, the salt of migalastat should be pharmaceutically acceptable. Suitable pharmaceutically acceptable salts will be apparent to those skilled in the art. Pharmaceutically acceptable salts include those described by Berge, Bighley and Monkhouse *J. Pharm. Sci* (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of migalastat and are included within the scope of this invention. In one embodiment of the invention migalastat is isolated as migalastat hydrochloride.

Migalastat may form acid addition salts with one or more equivalents of the acid. The present invention includes within its scope the use of migalastat in all possible stoichiometric and non-stoichiometric forms.

Migalastat may be prepared in crystalline or non-crystalline form and, if crystalline, may optionally be solvated, e.g. as the hydrate. This invention includes within its scope stoichiometric solvates (e.g. hydrates) as well as migalastat containing variable amounts of solvent (e.g. water). In addition, different crystallisation conditions may lead to the formation of different polymorphic forms of crystalline products. The present invention includes within its scope the use of migalastat in any polymorphic form.

Since the invention relates to the use of migalastat in pharmaceutical compositions it will readily be understood that the compound is preferably provided in substantially pure form, for example at least 60% pure, more suitably at least 75% pure and preferably at least 85%, especially at least 98% pure (% are on a weight for weight basis). Impure preparations of the compound may be used for preparing the more pure forms used in the pharmaceutical compositions.

The invention also provides migalastat produced in accordance with the processes of the invention, or a pharmaceutically acceptable salt thereof, for use in therapy. The invention provides a method for the treatment or prophylaxis of Fabry's disease, in a subject in need thereof, comprising administering to said subject an effective amount of migalastat produced in accordance with the processes of the invention, or a pharmaceutically acceptable salt thereof.

The invention also provides the use of migalastat produced in accordance with the processes of the invention, or a pharmaceutically acceptable salt thereof, in the manufacture of a medicament for use in the treatment or prophylaxis of Fabry's disease. For use in therapy migalastat is usually administered as a pharmaceutical composition.

Migalastat, or its pharmaceutically acceptable salts, may be administered by any convenient method, e.g. by oral, parenteral, buccal, sublingual, nasal, rectal or transdermal administration, and the pharmaceutical compositions adapted accordingly.

Migalastat or its pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered once or more than once a day, for example two or three a day. Such therapy may extend for a number of weeks or months. The dose and regimen may be selected from the following: 25 mg b.i.d; 50 mg once a day; 50 mg b.i.d; 50 mg once every other day; 75 mg once a day; 75 mg b.i.d; 100 mg once a day; 100 mg b.i.d; 150 mg once a day; 150 mg b.i.d; 150 mg once every other day; 250 mg once a day; 250 mg b.i.d; and 250 mg once every other day. In a specific embodiment the dose and regimen is 150 mg once every other day. In one specific embodiment the dose and regimen is 150 mg migalastat HCl once every other day.

It is to be understood that as used herein any reference to treatment includes both treatment of established symptoms and prophylactic treatment.

In another aspect of the present invention migalastat, its salts and/or pharmaceutical compositions may be used in combination with another therapeutically active agent. In one embodiment, migalastat produced according to the processes of the invention may be used in combination with replacement α-galactosidase A enzyme (α-Gal A) for the treatment of Fabry disease. Two α-Gal A products are currently available for the treatment of Fabry disease: agalsidase alfa (Replagal®, Shire Human Genetic Therapies) and agalsidase beta (Fabrazyme®, Genzyme Corporation).

The combinations referred to above may conveniently be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or combined pharmaceutical composition(s).

The invention also provides a method of preparing a combination as defined herein, the method comprising either (a) preparing a separate pharmaceutical composition for administration of the individual compounds of the combination either sequentially or simultaneously, or (b) preparing a combined pharmaceutical composition for administration of the individual compounds of the combination simultaneously, wherein the pharmaceutical composition comprises the combination together with one or more pharmaceutically acceptable carriers and/or excipients.

The present invention will now be described with reference to the following specific, non-limiting examples.

Example 1: Use of GCase Assay to Identify Microorganisms Producing DGJ and Galactostatin For biochemical detection of DGJ and galactostatin, several glycosidase assays from commercial sources were set up i.e.: α-galactosidase from green coffee beans and α-glucosidase from rice. These assays measured enzyme activity, using the corresponding 4-nitrophenyl-α-D-glycopyranoside as substrate at acid pH. The reaction is terminated after 1 h at room temperature by the addition of sodium carbonate; subsequent formation of 4-nitrophenolate at basic pH in each well is measured by absorbance (Abs) at 400 nm using a 384 w microplate reader. These assays were validated using several iminosugars from commercial sources.

Piperidine iminosugars are very polar and hence can be detected in extracellular media of cultures in this assay. Each strain was grown in 250 ml Erlenmeyer flasks containing 50 ml of culture media, at 28° C. in an orbital shaker at 200 rpm. After 4 fermentation days, culture broths were transferred to 50 ml Falcon and centrifuged for 20 min at 3000 rpm and then stored at 4° C.

The screening samples, comprising the supernatants obtained by centrifugation of culture broths, were tested at 10% final assay concentration, in duplicate, against α-galactosidase and α-glucosidase.

Supernatants inhibiting the α-galactosidase assay were further analyzed by LC/MS (uPLC-coupled to a triple quadrupole) using a HILIC column, eluted with a water/acetonitrile containing 0.1% formic acid gradient at 0.6 ml/min at 40° C. This analytical method quantifies the amount of 1-deoxygalactonojirimycin in culture broths with respect to the corresponding commercial standard up to 0.5 ppb, however the amount of galactostatin was determined as 1-deoxygalactonojirimycin equivalent.

During the screening of a microbial collection a total of 13 actinomycetes strains were identified as producers of 1-deoxygalactonojirimycin and/or galactostatin. Table 1 reports those strains and Streptomyces lydicus ATCC_31975 as reference strain.

TABLE 1

Actinomycetes identified from the microbial screening as DGJ and/or galactostatin producers

| Strain | Taxonomy |
| --- | --- |
| BTA122 | Unknown Actinomycete |
| BTA293 | Unknown Actinomycete |
| BTA530 | Streptomyces sp NCIMB 42142 |
| BTA1002 | Unknown Actinomycete |
| BTA1088 | Unknown Actinomycete |
| BTA1516 | Unknown Actinomycete |
| BTA1539 | Streptomyces lydicus ATCC_31975 |
| BTA1836 | Streptoverticillium roseoverticillatum |
| BTA1964 | Streptoverticillium reticulum |
| BTA2016 | Streptomyces fervens |
| BTA2024 | Streptoverticillium salmonis |
| BTA2052 | Streptoverticillium species |
| BTA2348 | Streptomyces fervens |
| BTA2474 | Streptoverticillium baldacii |

Example 2: Fermentation 1 l DGJ (a) Preparation of Streptomyces sp Spore Stock

Streptomyces sp NCIMB 42142 was grown at 26° C. with 40% humidity on agar containing Dextrin 0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%, for 9 to 11 days. The spores were removed and suspended in 10% sucrose and stored at circa −70° C. When required aliquots were thawed at room temperature and diluted to give the required concentration using Triton X/Saline (0.05% TritonX 100, 0.85% NaCl).

(b) Preparation and Inoculation of Seed Stage Fermentation

3 Lts seed medium was prepared by batching 2.5% Arcon F (a protein source), 2.0% dextrin, 0.25% magnesium sulphate, 0.1% potassium di-hydrogen orthophosphate, 0.1% Rape seed oil, 0.02% Calcium chloride, 0.02% Magnesium chloride, 0.02% Sodium chloride, 0.01% Iron chloride, 0.001% Zinc chloride, 0.001% Copper chloride, 0.001% Manganese sulphate into a batching vessel. The medium was pH adjusted to 7.7 with sodium hydroxide, 100 ml volume was dispensed into 500 ml shakeflasks and sterilised for 20 minutes at 121° C. 1.0 mLs of spores to provide a final concentration of $6 \times 10^4$/mL was introduced to each seed flask and incubated at 28° C. and 220 rpm for 48 hours.

(c) Preparation and Inoculation of Final Stage Fermentation

19 Lts final stage medium was prepared by batching 2.5% Cotton seed flour (a protein source), 1.7% lactose, 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 30 minutes and 1.4 Lts transferred to each sterile final stage vessels ready for inoculation with seed from the seed flasks.

The final stage vessels were set to 1400 rpm, 1.1 L/min air flow, 28° C. and the medium was not pH adjusted post sterilisation.

40 mls of seed grown for 48 hours was transferred into each of the final stage vessels and incubated under the above conditions for 214 hours. Dissolved oxygen levels are not monitored or maintained at this scale.

The final stage fermentations were monitored for pH, viscosity and production of migalastat throughout and harvested when migalastat concentrations levelled at 1700 ug/ml.

Example 3: Fermentation Scale Up 10 l DGJ (a) Preparation of *Streptomyces* sp Spore Stock

*Streptomyces* sp NCIMB 42142 was grown at 26° C. with 40% humidity on agar containing Dextrin 0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%, for 9 to 11 days. The spores were removed and suspended in 10% sucrose and stored at circa −70° C. When required aliquots were thawed at room temperature and diluted to give the required concentration using Triton X/Saline (0.05% TritonX 100, 0.85% NaCl).

(b) Preparation and Inoculation of Seed Stage Fermentation

19 Lts seed medium was prepared by batching 2.12% Arcon F (a protein source), 0.194% Foam Doctor (antifoam agent), 1.82% dextrin, 0.323% magnesium sulphate, 0.0364% potassium di-hydrogen orthophosphate, 0.0971% Rape seed oil and 0.0607% calcium carbonate into a batching vessel. The medium was pH adjusted to 7.8 with sodium hydroxide, sterilised for 40 minutes at 121° C. and 4 Lts transferred to sterile seed vessels ready for inoculation.

The seed vessel was set to 300 rpm, 2 L/min air flow, 28° C. and the medium was not pH adjusted post sterilisation.

10 mLs of spores to give a final concentration of $6 \times 10^4$ spores per mL in the seed vessel was introduced to the seed vessel and incubated at the above conditions for 54 hours.

(c) Preparation and Inoculation of Final Stage Fermentation

250 Lts final stage medium was prepared by batching 2.5% Cotton seed flour (a protein source), 1.7% lactose, 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 30 minutes and 10 Lts transferred to each sterile final stage vessel ready for inoculation with seed from the seed vessels.

The final stage vessels were set to 300 rpm, 10 L/min air flow, 28° C. and the medium was not pH adjusted post sterilisation.

250 mls of seed grown for 54 hours was transferred into each of the final stage vessels and incubated under the above conditions for 214 hours. Dissolved oxygen levels were maintained above 20% throughout the fermentation via agitation ramps.

The final stage fermentations were monitored for pH, viscosity and production of migalastat throughout and harvested when migalastat concentrations levelled at 1500 ug/ml.

Example 4: Fermentation Scale Up 1000/3000 l DGJ (a) Preparation of *Streptomyces* sp Spore Stock

*Streptomyces* sp NCIMB 42142 was grown at 26° C. with 40% humidity on agar containing Dextrin 0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%, for 9 to 11 days. The spores were removed and suspended in 10% sucrose and stored at circa −70° C. When required aliquots were thawed at room temperature and diluted to give the required concentration using Triton X/Saline (0.05% TritonX 100, 0.85% NaCl).

(b) Preparation and Inoculation of Seed Stage Fermentation

1000 Lts seed medium was prepared by batching 2.12% Arcon F (a protein source), 0.194% Foam Doctor (antifoam agent), 1.82% dextrin, 0.323% magnesium sulphate, 0.0364% potassium di-hydrogen orthophosphate, 0.0971% Rape seed oil and 0.0607% calcium carbonate into a batching vessel. The medium was pH adjusted to 7.8 with sodium hydroxide and sterilised for 40 minutes at 121° C. and transferred to the sterile seed vessel ready for inoculation.

The seed vessel was set to 80 rpm, 30 Nm$^3$/Hr air flow, 0.7 bar pressure, 28° C. and the medium was not pH adjusted post sterilisation.

500 mLs of spores at a concentration of $6 \times 10^4$/mL was introduced to the seed vessel via an inoculation can and incubated at the above conditions for 52 hours.

(c) Preparation and Inoculation of Final Stage Fermentation

2×3000 Lts final stage medium was prepared by batching 2.5% Cotton seed flour (a protein source), 1.7% lactose, 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 40 minutes and transferred to two sterile final stage vessels ready for inoculation with seed from the seed vessel.

The final stage vessels were set to 70 rpm, 110 Nm$^3$/Hr air flow, 0.7 bar pressure, 28° C. and the medium was not pH adjusted post sterilisation.

90 Lts of seed grown for 52 hours from the seed vessel was transferred into each of the final stage vessels via a sterile transfer line and incubated under the above conditions for 282 hours. Dissolved oxygen levels were maintained above 20% throughout the fermentation. The final stage fermentations were monitored for pH, viscosity and production of migalastat throughout and harvested when migalastat concentrations levelled at 1300 ug/ml.

(d) Removal of Broth Solids by Ultrafiltration

A flat sheet configured 10 kDa membrane has been successfully employed for this duty Product recovery may be enhanced by diafiltration at this stage.

(e) Removal of High MWt Materials

Permeate (+any diafiltrate) from the above UF stage is further ultrafiltered using 1 kDa membrane. A significant amount of colour reduction is achieved in the 1 kDa permeate. Again product recovery may be enhanced by diafiltration.

(f) Fractionation

Permeate from 1 kDa ultrafiltration is loaded onto a column of cation exchange resin (UBK550) which captures the migalastat product. Following a displacement wash with de-ionised water, migalastat is eluted from the resin using a step gradient of hydrochloric acid. The step gradient gives some separation of impurities from product.

(g) Work-Up of Pooled Fractions

Pooled fractions are pH adjusted into the range 6 to 7 by addition of solid anion exchange resin (IRA67) with good mixing. (This avoids the addition of titrant (e.g.: NaOH) which leads to an undesirable level of additional inorganics in the liquor). Anion exchange resin is removed by filtration, washed to remove entrained rich migalastat solution and then regenerated pending another process cycle. Filtrate is progressed to concentration step.

(h) Concentration of Pooled Fractions pH adjusted pooled fractions are concentrated by nanofiltration (aka reverse Osmosis). Final concentration of migalastat achievable by this process is equipment and membrane dependent. Large scale trials indicate that concentrated pooled fractions containing 30 to 40 mg/ml in addition to other impurities present at this stage have an osmotic pressure of approximately 40 barg. Equipment with a high operating pressure would facilitate removal of further water to a higher migalastat titre. The final desired concentration may only be achievable by evaporation.

Example 5: Migalastat HCl Salt Isolation

All weights, volumes and equivalents are relative to the free base
(a) Pre-Filtration
An aqueous solution of migalastat free base is assayed and the mass of migalastat free base in solution was determined. The free base aqueous solution (equivalent to 1.0 wt of Migalastat free base) is filtered through a GF type filter (1.2 µm) and the filtrate charged to a rotary evaporator flask.
(b) Distillation and Acid Digestion
The contents are then concentrated under vacuum (jacket temperature ca. 45° C.) to approx. 1.8 weights wrt free base input. The contents are cooled to 20-25° C. and then 36-37% w/w hydrochloric acid (19.5 eq=10 vol) is added. The contents are then warmed to 45-50° C. and stirred for ca. 30 minutes. The resultant slurry is filtered at ca. 30-35° C. to recover the precipitated sodium chloride. The flask and cake are washed with 36-37% w/w hydrochloric acid (1.2 eq=0.6 vol).
(c) Crystallisation
The filtrate is transferred to the crystallisation vessel and cooled to 15-20° C. Absolute ethanol (25 vol) is added over at least 30 minutes to the crystallisation vessel at 15-25° C. to give a slurry. The contents stirred at ca. 20° C. for at least 1 h.
The product is filtered off and washed with absolute ethanol (2×2.5 vol), and the product is sucked free of solvent. The product is then dried at ≤40° C. until a constant weight is achieved.
Expected yield: 80-90% theory
Percent Yield Range Observed: 80-90% Theory
$V_{min}$=2 vol
$V_{max}$=37 vol Example 6: Fermentation of Galactostatin (a) Preparation of *Streptomyces lydicus* ATCC319075 Spore Stocks
*Streptomyces lydicus* ATCC 317095 was grown at 26° C. with 40% humidity on agar containing Dextrin0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%, for 5 to 7 days. The spores were removed and suspended in 10% sucrose and stored at circa −70° C. When required aliquots were thawed at room temperature and diluted to give the required concentration using Triton X/Saline (0.05% triton 0.85% NaCl).
(b) Preparation and Inoculation of Seed Stage Fermentation
3 Lts seed medium was prepared by batching 2.5% Arcon F (a protein source), 2.0% dextrin, 0.25% magnesium sulphate, 0.1% potassium di-hydrogen orthophosphate, 0.1% Rape seed oil, 0.02% Calcium chloride, 0.02% Magnesium chloride, 0.02% Sodium chloride, 0.01% Iron chloride, 0.001% Zinc chloride, 0.001% Copper chloride, 0.001% Manganese sulphate into a batching vessel. The medium was pH adjusted to 7.7 with sodium hydroxide, 100 ml volume was dispensed into 500 ml shakeflasks and sterilised for 20 minutes at 121° C.

1.0 mLs of spores at a concentration of $6 \times 10^4$/mL was introduced to each seed flask and incubated at 28° C. and 220 rpm for 48 hours.
(c) Preparation and Inoculation of Final Stage Fermentation
19 Lts final stage medium was prepared by batching 2.5% Cotton seed flour (a protein source), 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 30 minutes and 1.4 Lts transferred to each sterile final stage vessels ready for inoculation with seed from the seed flasks.
The final stage vessels were set to 1400 rpm, 1.1 L/min air flow, 28° C. and the medium was not pH adjusted post sterilisation.
40 mls of seed grown for 48 hours was transferred into each of the final stage vessels and incubated under the above conditions for 214 hours. Dissolved oxygen levels are not monitored or maintained at this scale.
The final stage fermentations were monitored for pH, viscosity and production of galactostatin throughout and harvested when galactostatin concentrations reached 1700 ug/ml.

Example 7: Preparation of migalastat, (2R,3S,4R, 5S)-2-(hydroxymethyl)piperidine-3,4,5-triol, from galactostatin bisulfate, (2S,3R,4S,5S,6R}-3,4,5-trihydroxy-6-(hydroxymethyl)piperidine-2-sulfonic acid To a suspension of Galactostatin bisulfate, (2S,3R,4S,5S, 6R)-3,4,5-trihydroxy-6-(hydroxymethyl)piperidine-2-sulfonic acid, (50 mg, 0.206 mmol) in methanol (3 mL) was added acetic acid (2.5 eqs, 29 µL, 0.514 mmol) and Adam's Catalyst (PtO$_2$, 20 mg). The mixture was hydrogenated at 40° C. and 5.5 bar pressure for 18 h before being vented. The crude mixture was then filtered to remove the catalyst and other insoluble's and the filtrate concentrated to dryness under reduced pressure to give (2R,3S,4R,5S)-2-(hydroxymethyl)piperidine-3,4,5-triol, acetate (11 mg, 0.067 mmol, 24%) as an off white solid. $^1$H NMR: δ (400 MHz, D$_2$O): 4.21-4.18 (1H, m, CH$_{eq}$), 4.11 (1H, ddd, J=5.0, 10.0, 12.0 Hz, CH$_{ax}$), 3.91 (1H, dd, J=5.0, 12.0 Hz, CH$_a$H$_b$), 3.83 (1H, dd, J=9.0, 12.0 Hz, CH$_a$H$_b$), 3.66 (1H, dd, J=2.0, 10.0 Hz, CH$_{ax}$), 3.54 (1H, dd, J=5.0, 12.0 Hz, CH$_{eq}$), 3.44 (1H, dd, J=5.0, 9.0 Hz, CH$_{ax}$), 2.90 (1H, app. t, J=12.0 Hz, CH$_{ax}$).

Example 8: Fermentation 1 1 DGJ Using Lactulose (a) Preparation of *Streptomyces* sp Spore Stock
Surface growth of BTA530 Y3 growing on 0.5% Yeast Extract, 1.0% Malt Extract, 0.5% glycerol, and 2% Bacto agar pH7.3 was streaked out onto agar which promotes spore formation (Dextrin 0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%.). After 9-11 days incubation at 26° C. with 40% humidity the spores were stripped off and suspended in 10% sucrose. The spore suspension was used as a Master Stock (MS) and stored in 1.2 mL volumes at circa −70° C.
MS frozen spores were thawed at room temperature and used to inoculate Thompson Bottles containing the agar above or a similar one omitting the dextrin. After 9-11 days incubation 26° C. with 40% humidity the Bottles were placed at 4° C. for 18-48 hours. The spores were stripped off the surface of the agar, suspended in 10% sucrose and stored at circa −70° C. in 1.2, 5 or 15 mL volumes until required as inoculum for the fermentation vessels (b) Preparation and Inoculation of Seed Stage Fermentation 3 Lts seed medium was prepared by batching 2.5% Cotton seed flour (a protein source), 1.5% Meritose (dextrose), 4% dextrin, 0.5% CSL (a protein source), 0.8% calcium carbonate, into a batching vessel. The medium was pH adjusted to 7.2 with sodium hydroxide, 100 ml volume was dispensed into 500 ml shakeflasks and sterilised for 20 minutes at 121° C. BTA530 Y3 spore stock was diluted using Triton X and 1 ml added to the seed flasks to give a concentration of $1.5 \times 10^7$ spores per mL in each seed flask. Flasks were incubated at 28° C. and 220 rpm for 48 hours.

(c) Preparation and Inoculation of Final Stage Fermentation

19 Lts final stage medium was prepared by batching 2.5% Cotton seed flour (a protein source), 1.7% lactulose, 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 30 minutes and 1.4 Lts transferred to each sterile final stage vessels ready for inoculation with seed from the seed flasks.

The final stage vessels were set to 1400 rpm, 1.1 L/min air flow, 28° C. and the medium was not pH adjusted post sterilisation.

40 mls of seed grown for 48 hours was transferred into each of the final stage vessels and incubated under the above conditions for 214 hours. Dissolved oxygen levels are not monitored or maintained at this scale.

The final stage fermentations were monitored for pH, viscosity and production of migalastat throughout and harvested when migalastat concentrations levelled at 1700 ug/ml.

Example 9: Fermentation 1 1 DGJ Using Mutated *Streptomyces* sp (a) Preparation of *Streptomyces* sp Spore Stock

*Streptomyces* sp mutant BTM4 (NCIMB 42358) was grown at 26° C. with 40% humidity on agar containing Dextrin 0.3%, Trehalose dihydrate 1%, K2HPO4 0.05%, NaCl 0.1%, MgSO4.7H2O 0.1%, CaCl2 0.05%, Casamino acids 0.2%, MOPS buffer 1.05%, FeSO4 0.0001%, MnSO4.H2O 0.000076%, ZnSO4.7H2O 0.0001%, ROKO agar 3%, for 9 to 11 days. The spores were removed and suspended in 10% sucrose and stored at circa −70° C. When required aliquots were thawed at room temperature and diluted to give the required concentration using Triton X/Saline (0.05% TritonX 100, 0.85% NaCl).

(b) Preparation and Inoculation of Seed Stage Fermentation

3 Lts seed medium was prepared by batching 2.5% Arcon F (a protein source), 2.0% dextrin, 0.25% magnesium sulphate, 0.1% potassium di-hydrogen orthophosphate, 0.1% Rape seed oil, 0.02% Calcium chloride, 0.02% Magnesium chloride, 0.02% Sodium chloride, 0.01% Iron chloride, 0.001% Zinc chloride, 0.001% Copper chloride, 0.001% Manganese sulphate into a batching vessel. The medium was pH adjusted to 7.7 with sodium hydroxide, 100 ml volume was dispensed into 500 ml shakeflasks and sterilised for 20 minutes at 121° C.

1.0 mLs of spores to provide a final concentration of $6 \times 10^4$/mL was introduced to each seed flask and incubated at 28° C. and 220 rpm for 48 hours.

(c) Preparation and Inoculation of Final Stage Fermentation

19 Lts final stage medium was prepared by batching 2.5% Cotton seed flour (a protein source), 1.7% lactose, 1.5% Meritose, 4% glycerol, 0.5% CSL (a protein source), 0.8% calcium carbonate and 0.1% Foam Doctor (antifoam agent) into a batching vessel. The medium was pH adjusted to 7.2 with sodium hydroxide and then sterilised at 121° C. for 30 minutes and 1.4 Lts transferred to each sterile final stage vessels ready for inoculation with seed from the seed flasks.

The final stage vessels were set to 1400 rpm, 1.1 L/min air flow, 28° C. and the medium was not pH adjusted post sterilisation.

40 mls of seed grown for 48 hours was transferred into each of the final stage vessels and incubated under the above conditions for 214 hours. Dissolved oxygen levels are not monitored or maintained at this scale.

The final stage fermentations were monitored for pH, viscosity and production of migalastat throughout and harvested when migalastat concentrations levelled at 2400 ug/ml.

The invention claimed is:

1. A process for the production of migalastat, said process comprising the steps of: (a) culturing a microorganism under conditions, wherein said culturing is carried out by a fermentation process chosen from the group of: batch fermentation; fed-batch fermentation; and continuous fermentation, such that migalastat is produced, and (b) detecting and/or isolating migalastat, wherein said microorganism is chosen from: *Streptomyces* sp BTA530 (NCIMB 42142) and *Streptomyces* sp mutant BTM4 (NCIMB 42358).

2. The process as claimed in claim 1, wherein said detecting step (b) is carried out using an α-galactosidase A activity assay.

3. The process as claimed in claim 1, wherein said microorganism is cultured in a medium comprising lactose.

* * * * *